US008066661B2

United States Patent
Boyd et al.

(10) Patent No.: US 8,066,661 B2
(45) Date of Patent: Nov. 29, 2011

(54) VISCOUS FORMULATIONS AND THEIR USE IN NEEDLE-FREE INJECTION

(75) Inventors: Brooks M. Boyd, Berkeley, CA (US); Sujata Mudumba, Hayward, CA (US); Stephen J. Farr, Orinda, CA (US)

(73) Assignee: Zogenix, Inc., Emeryville, CA (US)

( * ) Notice: Subject to any disclaimer, the term of this patent is extended or adjusted under 35 U.S.C. 154(b) by 184 days.

(21) Appl. No.: 12/032,044

(22) Filed: Feb. 15, 2008

(65) Prior Publication Data
US 2008/0214995 A1 Sep. 4, 2008

Related U.S. Application Data (63) Continuation-in-part of application No. PCT/US2006/044778, filed on Nov. 16, 2006.

(60) Provisional application No. 60/738,089, filed on Nov. 17, 2005.

(51) Int. Cl.
*A61M 5/30* (2006.01)

(52) U.S. Cl. ............. 604/68; 604/69; 604/70; 604/71; 604/72

(58) Field of Classification Search ............ 604/68–72
See application file for complete search history.

(56) References Cited

U.S. PATENT DOCUMENTS

| | | | | |
|---|---|---|---|---|
| 5,891,086 | A  * | 4/1999  | Weston | 604/70 |
| 7,615,234 | B2   | 11/2009 | Potter et al. | |
| 2001/0002434 | A1 * | 5/2001  | Lubrecht | 604/232 |
| 2004/0024350 | A1 * | 2/2004  | Brouillette | 604/68 |
| 2004/0215135 | A1 * | 10/2004 | Sheldrake et al. | 604/68 |
| 2005/0192530 | A1 * | 9/2005  | Castellano | 604/70 |
| 2006/0083768 | A1 * | 4/2006  | Labrecque et al. | 424/423 |
| 2007/0093440 | A1 * | 4/2007  | Champion et al. | 514/44 |
| 2007/0167907 | A1 * | 7/2007  | Deslierres et al. | 604/68 |

FOREIGN PATENT DOCUMENTS
CN 100425298 10/2008

* cited by examiner

*Primary Examiner* — Nicholas Lucchesi
*Assistant Examiner* — Ian Holloway
(74) *Attorney, Agent, or Firm* — Karl Bozicevic; Bozicevic, Field & Francis LLP (57) ABSTRACT

Formulations are described that are viscous and will benefit from needle-free delivery at high driving pressures. Conventional delivery of these viscous formulations by hypodermic syringes is inconvenient as well as painful. Formulations include those which have a viscosity of about 5 cS or more at about 20° C. and which can have 0.5 ml or more administered by a needle-free injector in about 0.1 second±0.02 seconds.

4 Claims, 3 Drawing Sheets

VISCOUS FORMULATIONS AND THEIR USE IN NEEDLE-FREE INJECTION

CROSS-REFERENCE

This application is a continuation-in-part application of International Application Serial No. PCT/US2006/044778 filed Nov. 16, 2006, which application claims priority to Provisional Application Ser. No. 60/738,089 filed Nov. 17, 2005, which are incorporated herein by reference in their entirety noting that the current application controls to the extent there is any contradiction with any earlier applications and to which applications we claim priority under 35 USC §119 and 120.

FIELD OF THE INVENTION

The present invention relates to various classes of viscous formulations and the delivery via needle-free injection for parenteral and other pharmaceutical applications.

BACKGROUND OF THE INVENTION

Modern drug development has shown that the market for injectable drugs is growing, since the majority of these molecules are too large and fragile to be delivered by other methods such as orally. However, it is difficult to formulate many of these molecules into stable solutions that are sufficiently concentrated to inject an efficacious amount in a reasonable sized dose (<1 ml). As a result, the formulation may be quite viscous, often up to 10,000 times thicker than water i.e. 10,000 cS (centistokes) or higher. Also, the advent of controlled release strategies has opened new areas for development and delivery of formulations. For parenteral applications, the viscosity of enhanced formulations has been an issue with several controlled release formulations. Liquids with viscosities significantly higher than water become increasingly difficult, if not impractical, to inject as viscosity increases using a conventional needle and syringe.

Viscous formulations containing polymers, for example, are employed for the controlled release of drugs after Intravenous (IV) subcutaneous (SC), intra-dermal (ID) or intramuscular (IM) injection. These formulations are notoriously difficult to inject, requiring a large force to be delivered by the hand of the care-giver, and often quite painful for the patient. The force required for injection is associated with viscous drag of the formulation while traversing the length of the needle. Consequently, large bore needles are employed (creating even greater levels of pain), but still the injection time can be in the order of minutes or more.

The ability to inject a drug incorporated into a polymer to a localized site and have the polymer form a semi-solid drug depot has a number of advantages. Among these advantages is ease of application localized delivery, prolonged drug delivery, and better compliance with prescribed therapy due to less frequent dosing. The better compliance is very important for delivery of psychiatric drugs, wherein the disease state can make compliance difficult or impossible, and a depot can allow for infrequent, e.g. monthly, dosing in a clinical setting. For these reasons a large number of in situ setting polymeric delivery systems have been developed and investigated for use in delivering a wide variety of drugs.

Currently, there are few synthetic or natural polymeric materials which can be used for the controlled delivery of drugs, including peptide and protein drugs, because of the strict regulatory compliance requirements, such as biocompatibility, clearly defined degradation pathway, and safety of the degradation products. The most widely investigated and advanced biodegradable polymers in regard to available toxicological and clinical data are the aliphatic poly(.alpha.-hydroxy acids), such as poly(D,L- or L-lactic acid) (PLA) and poly(glycolic acid) (PGA) and their copolymers (PLGA). These polymers are commercially available and are presently being used in medical products, for example as bioresorbable sutures. An FDA-approved system for controlled release of leuprolide acetate, the Lupron Depot™, is also based on PLGA copolymers. The Lupron Depot. consists of injectable microspheres, which release leuprolide acetate over a prolonged period (e.g., about days) for the treatment of prostate cancer.

A. S. Sawhney and J. A. Hubbell, J. Biomed. Mat. Res., 24, 1197-1411 (1990), synthesized terpolymers of D,L-lactide, glycolide and c-caprolactone which degrade rapidly in vitro. The hydrophilicity of the material was increased by copolymerization with a poloxamer surfactant (Pluronic F-68). This poloxamer is a block copolymer comprising about 80% by weight of a relatively hydrophobic poly(oxypropylene) block and 20% by weight of a hydrophilic poly(oxyethylene) block. Copolymerization with the poloxamer resulted in a stronger and partly crystalline material which was mechanically stable at physiological temperatures (e.g. 37.degree. C.) in water.

One system, which can be fabricated in aqueous solution, is a class of block copolymers referenced above and marketed under the Pluronic™. tradename. These copolymers are composed of two different polymer blocks, i.e. hydrophilic poly(oxyethylene) blocks and hydrophobic poly(oxypropylene) blocks to make up a triblock of poly(oxyethylene)-poly(oxypropylene)-poly(oxyethylene). The triblock copolymers absorb water to form gels which exhibit reverse thermal gelation behavior.

Churchill et al, U.S. Pat. Nos. 4,526,938 and 4,745,160 show copolymers that are either self-dispersible or can be made self-dispersible in aqueous solutions. These copolymers are ABA triblock or AB block copolymers composed of hydrophobic A-blocks, such as polylactide (PLA) or poly(lactide-co-glycolide) (PLGA), and hydrophilic B-blocks, such as polyethylene glycol (PEG) or polyvinyl pyrrolidone.

Dunn et al, in U.S. Pat. No. 5,324,519, disclose the composition of a liquid formulation of a thermoplastic polymer and a pharmaceutically acceptable organic solvent (trade name Atrigel). The composition is administered as a liquid to an implant site, whereupon the solvent diffuses or dissipates into the surrounding aqueous tissue fluids. The thermoplastic polymer is not soluble in these aqueous fluids so that it coagulates or solidifies to form a microporous solid or gelatinous matrix. The composition is a liquid formulation of a thermoset prepolymer or copolymer, preferably an acrylic ester-terminated biodegradable prepolymer, which is capable of cross-linking in situ to form a polymeric or copolymeric solid or gelatinous matrix.

In U.S. Pat. No. 6,117,949, Rathi et al. disclose A water soluble biodegradable ABA- or BAB-type triblock polymer is disclosed that is made up of a major amount of a hydrophobic polymer made of a poly(lactide-co-glycolide) copolymer or poly(lactide) polymer as the A-blocks and a minor amount of a hydrophilic polyethylene glycol polymer B-block, that possesses reverse thermal gelation properties.

U.S. Pat. No. 5,980,948 describes a composition comprised of a product including a biologically active agent encapsulated in a matrix comprising a polyetherester copolymer, such as a polyethylene glycol terephthalate/polybutylene terephthalate copolymer. The polyetherester copolymer protects the biologically active agent (including proteins, peptides, and small drug molecules) from degradation or denaturation.

U.S. Pat. No. 5,747,058 describes a delivery system in situ which uses sucrose acetate isobutyrate (SAIB). Sucrose acetate isobutyrate is a highly lipophilic sugar derivative, which is currently used as stabiliser and emulsifying agent to human diets in the Food Industry. This technology, called SABER™, was patented by Tipton and Richard (Southern Biosystems, Inc.) in 1995. The high viscosity of the liquid sucrose acetate isobutyrate carrier is lowered by the addition of a water soluble or miscible solvent such as ethanol or dimethylsulfoxide. After addition of the drug, the composition is injected and forms a highly viscous implant in situ, which releases the drug over time.

EP 1184032 describes a method for producing hydrogels, based on crystallization of dextran or derivatives thereof. These hydrogels find use in pharmaceutical, medical and biotechnological applications, e.g. as controlled release systems for the delivery of active ingredients in in vivo and in vitro applications. The hydrogels according to the present invention are priced by crystallization from an aqueous solution that is essentially free of organic solvents or crystallization enhancers.

EP0842657 describes a two phase controlled release system containing dextran and polyethylene glycol. EP0941068 describes a two phase dextran containing controlled release system for proteins.

Many of these and other controlled release formulations are limited by their elevated viscosity, which leads to many delivery difficulties, such as high required hand strength, long delivery times, and pain and fear associated with the large bore needle. Thus, there is a need to deliver these compounds in a rapid, automated fashion without a needle.

Needle-free injectors are available using many different types of energy, and the energy may be supplied by the user, for example where a spring is manually compressed and latched to temporarily store the energy until it is required to "fire" the injector. Alternatively, the injector may be supplied having the energy already stored—for instance by means of a precompressed spring (mechanical or gas), or pyrotechnic charge.

Some injectors are intended for disposal after a single use, whereas others have a re-loadable energy storage means and a disposable medicament cartridge, and there are many combinations to suit particular applications and markets. For the purposes of the present disclosure, the term "actuator" will be used to describe the energy storage and release mechanism, whether or not it is combined with the medicament cartridge. In all cases, it is necessary to arrange for sufficient force at the end of the piston stroke to deliver the entire medicament at the required pressure.

EP 0 063 341 and EP 0 063 342 disclose a needle-free injector which includes a piston pump for expelling the liquid to be injected, which is driven by a motor by means of a pressure agent. The liquid container is mounted laterally to the piston pump. The amount of liquid required for an injection is sucked into the pump chamber by way of an inlet passage and a flap check valve when the piston is retracted. As soon as the piston is moved in the direction of the nozzle body the liquid is urged through the outlet passage to the nozzle and expelled. The piston of the piston pump is a solid round piston.

EP 0 133 471 describes a needle-free vaccination unit which is operated with carbon dioxide under pressure, from a siphon cartridge by way of a special valve.

EP 0 347 190 discloses a vacuum compressed gas injector in which the depth of penetration of the injected drug can be adjusted by means of the gas pressure and the volume of the drug can be adjusted by way of the piston stroke.

EP 0 427 457 discloses a needle-free hypodermic syringe which is operated by means of compressed gas by way of a two-stage valve. The injection agent is disposed in an ampoule which is fitted into a protective casing secured to the injector housing. The ampoule is fitted on to the end of the piston rod. Disposed at the other end of the ampoule is the nozzle whose diameter decreases towards the end of the ampoule.

WO 89/08469 discloses a needle-free injector for one-off use. WO 92/08508 sets forth a needle-free injector which is designed for three injections. The ampoule containing the drug is screwed into one end of the drive unit, with the piston rod being fitted into the open end of the ampoule. At its one end, the ampoule contains the nozzle through which the drug is expelled. A displaceable closure plug is provided approximately at the center of the length of the ampoule. The dose to be injected can be adjusted by changing the depth of the ampoule. The piston rod which projects from the drive unit after actuation of the injector is pushed back by hand. Both units are operated with compressed gas.

WO 93/03779 discloses a needle-free injector with a two-part housing and a liquid container which is fitted laterally to the unit. The drive spring for the piston is stressed by means of a drive motor. The spring is released as soon as the two parts of the housing are displaced relative to each other by pressing the nozzle against the injection location. Respective valves are provided in the intake passage for the liquid and in the outlet of the metering chamber.

WO 95/03844 discloses a further needle-free injector. It includes a liquid-filled cartridge which at one end includes a nozzle through which the liquid is expelled. At the other end the cartridge is closed by a cap-type piston which can be pushed into the cartridge. A piston which is loaded by a pre-stressed spring, after release of the spring, displaces the cap-type piston into the cartridge by a predetermined distance, with the amount of liquid to be injected being expelled in that case. The spring is triggered as soon as the nozzle is pressed sufficiently firmly against the injection location. This injector is intended for one-off or repeated use. The cartridge is arranged in front of the spring-loaded piston and is a fixed component of the injector. The position of the piston of the injector which is intended for a plurality of uses is displaced after each use by a distance in a direction towards the nozzle. The piston and the drive spring cannot be reset. The pre stressing of the spring is initially sufficiently great to expel the entire amount of liquid in the cartridge all at once. The spring can only be stressed again if the injector is dismantled and the drive portion of the injector assembled with a fresh, completely filled cartridge.

U.S. Pat. No. 5,891,086 describes a needle-free injector, combining an actuator and a medicament cartridge. The cartridge is pre-filled with a liquid to be injected in a subject, and having a liquid outlet and a free piston in contact with the liquid, the actuator comprising an impact member urged by a spring and temporarily restrained by a latch means, the impact member being movable in a first direction under the force of the spring to first strike the free piston and then to continue to move the piston in the first direction to expel a dose of liquid through the liquid outlet, the spring providing a built-in energy store and being adapted to move from a higher energy state to a lower energy state, but not vice versa. The actuator may comprise trigger means to operate the said latch, and thus initiate the injection, only when a predetermined contact force is achieved between the liquid outlet of the said cartridge and the subject. Further examples and improvements to this needle-free injector are found in U.S. Pat. Nos. 6,620,135, 6,554,818, 6,415,631, 6,409,032, 6,280,410, 6,258,059, 6,251,091, 6,216,493, 6,179,583, 6,174,304, 6,149,625, 6,135,979, 5,957,886, 5,891,086, and 5,480,381, incorporated herein by reference.

U.S. Pat. No. 3,859,996, Mizzy, discloses a controlled leak method to ensure that the injector orifice is placed correctly at the required pressure on the subject's skin at the correct normal to the skin attitude. When placement conditions are met, controlled leak is sealed off by contact pressure on the subject's skin, the pressure within the injector control circuit rises until a pressure sensitive pilot valve opens to admit high pressure gas to drive the piston and inject the medicament.

WO Patent 82/02835. Cohen and Ep-A-347190, Finger, discloses a method to improve the seal between the orifice and the skin and prevent relative movement between each. This method is to employ a vacuum device to suck the epidermis directly and firmly onto the discharge orifice. The discharge orifice is positioned normal to the skin surface in order to suck the epidermis into the orifice. This method for injection of the medicament into the skin and the injector mechanism are different and do not apply to the present invention because of its unique ampule design.

U.S. Pat. No. 3,859,996, Mizzy, discloses a pressure sensitive sleeve on the injector which is placed on the subject, whereby operation of the injector is prevented from operating until the correct contact pressure between orifice and the skin is achieved. The basic aim is to stretch the epidermis over the discharge orifice and apply the pressurized medicament at a rate which is higher than the epidermis will deform away from the orifice.

U.S. Pat. No. 5,480,381, T. Weston, discloses a means of pressuring the medicament at a sufficiently high rate to pierce the epidermis before it has time to deform away from the orifice. In addition, the device directly senses that the pressure of the discharge orifice on the subject's epidermis is at a predetermined value to permit operation of the injector. The device is based on a cam and cam follower mechanism for mechanical sequencing, and contains a chamber provided with a liquid outlet for expelling the liquid, and an impact member, to dispell the liquid.

U.S. Pat. No. 5,891,086, T. Weston, describes a needle-free injector that contains a chamber that is pre-filled with a pressurized gas which exerts a constant force on an impact member in order to strike components of a cartridge and expulse a dose of medicament. This device contains an adjustment knob which sets the dose and the impact gap, and uses direct contact pressure sensing to initiate the injection.

A number of biologically-active agents in viscous formulations would benefit from being delivered using the needle-free injector. This group could consist of (but not limited to) anti-inflammatory agents, antibacterial agents, antiparasitic agents, antifungal agents, antiviral agents, anti-neoplastic agents, analgesic agents, anesthetics, vaccines, central nervous system agents, growth factors, hormones, antihistamines, osteoinductive agents, cardiovascular agents, anti-ulcer agents, bronchodilators, vasodilators, birth control agents and fertility enhancing agents, interferon alpha, growth hormone, osteoporosis drugs including PTH and PTH analogs and fragments, obesity drugs, psychiatric drugs, anti-diabetes, female infertility, AIDS, treatment of growth retardation in children, hepatitis, multiple sclerosis, migraine headaches, and allergic reactions.

SUMMARY OF THE INVENTION

The invention includes a device for the delivery of an active pharmaceutical ingredient which device is comprised of a needle-free injector comprised of a channel and one exit opening. The ratio of the channel length to the channel exit opening diameter is less than 10. The device is filled with a formulation which has viscosity of 5 cS or more at 20° C. and the formulation is comprised of a pharmaceutically active drug and a pharmaceutically acceptable carrier. In some embodiments the ratio of the length to the exit diameter is less than 7 and the viscosity of the formulation is 10 cS or more at 20° C.

The invention also includes a method of dispensing a formulation which includes loading a formulation into a needle-free delivery device comprising a channel and an exit opening with a channel length to exit opening diameter ratio of less than 10 where the formulation is comprised of a pharmaceutically active drug in a carrier and has a viscosity of 5 cS or more at 20° C. The loaded formulation is then extruded through the exit opening at a rate of 500 microliters or more per second and the rate may be 5,000 microliters or more per second.

The device of the present invention comprises an actuator for use in conjunction with a cartridge to form a needle-free injector, the cartridge being pre-filled with a liquid to be injected in a subject, the cartridge having a liquid outlet and a free piston inward of the liquid outlet in contact with the liquid, said actuator comprising:

(a) a housing having a forward portion adapted to be connected with the cartridge;

(b) impact member mounted within said housing inward of the forward portion so as to be movable from a first position toward the forward portion to strike the free piston when a cartridge is connected and to continue to move the free piston toward the liquid outlet whereby a dose of the liquid is expelled through the liquid outlet in the cartridge;

(c) a chamber within said housing pre-filled with pressurized gas and connected with said impact member such that said pressurized gas is constantly in communication with and constantly exerts a force on said impact member to normally urge said impact member toward the liquid outlet; and (d) a latch within said housing which engages said impact member to prevent movement of the impact member toward the forward portion in response to said force exerted by said pressurized gas, and being mounted to be movable out of engagement with said impact member to a firing position, in which said latch permits such movement.

In one formulation that would especially benefit from needle-free delivery, the biologically active agent is psychiatric drug, preferably an anti-psychotic drug for treatment of conditions such as schizophrenia or mania associated with bipolar disorder. Injectable, sustained release formulations of these compounds would lead to a great improvement in outcomes, as the subjects cannot reliably self medicate or present at a physicians office. Many compounds could be used with the present invention for the treatment of psychoses, including but not limited to Aripiprazole, Clozapine, Zyprasidone, Molindone, Quetiapine, Olanzapine, Risperidone, Paliperidone, Iloperidone, and pharmaceutically acceptable salts and ester forms thereof.

Risperidone has been previously delivered in a sustained release form, as described in U.S. Pat. Nos. 5,688,801, 5,770,231, 5,792,477, 5,916,598, 5,965,168, 6,110,503, 6,110,921, 6,194,006, 6,264,987, 6,368,632, 6,379,703, 6,379,704, 6,403,114, 6,534,092, and 6,596,316. These patents disclose a sustained release microparticle formulation of the Risperidone. Many improvements over this art is possible, including less frequent dosing, smaller injection volumes, no needle vs a fairly large, 20 gauge needle, immediate onset of action that does not require an oral 3 week loading dose, Extended stability with no requirement for reconstitution.

The requirement for a fairly large needle, 20 gauge or larger for the delivery of viscous formulations with a need and syringe, can be especially significant. Large needles can be very painful. They can also be visually intimidating, especially in patients ungoing psychotic episodes. Because of these issues, often the preferred needle is smaller than would otherwise be used, leading to long delivery times, and the requirement of significant hand strength on the part of the care giver. This often rules out the possibility of treatment in a home setting, either self treatment or by an relatively untrained care giver such as a family member. The inability to dose at home leads to higher costs of therapy and lower compliance.

An aspect of the invention is a desirable delivery time of high viscosity formulations via needleless injection.

Another aspect of the invention is acceptable pain associated with injection of high viscosity formulations.

Another aspect of the invention relates to fear of needles associated with injection of high viscosity formulations.

Another aspect of the invention relates to the danger of needle stick injury and cross-contamination associated with injection of high viscosity formulations.

Another aspect of the invention relates to the preparation associated with injection of high viscosity formulations, by supplying a pre-filled, single use disposable injector.

Another aspect of the invention relates to the drug release profile associated with injection of high viscosity depot formulation, especially surface eroding systems.

These and other aspects of the invention will become apparent to those persons skilled in the art upon reading the details of the devices and methodology as more fully described below.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

DETAILED DESCRIPTION OF THE INVENTION

Before the present devices, formulations and methods are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supercedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a formulation" includes a plurality of such formulations and reference to "the polymer" includes reference to one or more polymers and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions

Specific gravity: ratio of a compound's density to that of water.

Centipoise and centistokes: different measurements of viscosity, not just different units. Centipoise is a dynamic measurement of viscosity whereas centistoke is a kinematic measurement of viscosity. The conversion from centistoke and centipoise to s.i. units is given below:

$$1 \text{ cS}=0.0001 \text{ m}^2/\text{s} \quad 1 \text{ cP}=0.001 \text{ Ns/m}^2$$

Conversion from centistoke to centipoise:

$$\text{centipoise}=\text{centistoke} \times \text{density of liquid}$$

Formulation shall mean any liquid, solid, or other state of matter that can be injected. Preferred formulations are liquid formulations, including polymers and gels. Formulations include but are not limited to those containing excipients that are suitable for injection, and contain one or more active pharmaceutical ingredients. Aspects of the invention are generally apparent when using formulations with viscosities sufficiently high that the formulation can not administered by injection without significant problems.

A depot injection is an injection, usually subcutaneous, intravenous, or intramuscular, of a pharmacological agent which releases its active compound in a consistent way over a long period of time. Depot injections may be available as certain forms of a drug, such as decanoate salts or esters. Examples of depot injections include Depo Provera and haloperidol decanoate. Depots can be, but are not always, localized in one spot in the body.

Bulk erosion: The rate of water penetration into the depot exceeds the rate at which the depot is eroded (i.e. transformed into water soluble products)—leading to an erosion process that occurs throughout the entire volume of the depot—true with most hydrophilic polymers used in drug delivery currently.

Surface Erosion: The rate of water penetration into the depot is slower than the rate at which the depot is eroded—The depot starts eroding before water has penetrated the entire volume of the device.

"Biodegradable" means that the depot can chemically break down or degrade within the body to form nontoxic components. The rate of degradation can be the same or different from the rate of drug release.

s.i. units: international system of units
API: Active Pharmaceutical Ingredient or drug to inject using a hypodermic needle-free injector device. As shown within FIG. 3 a needle-free injector device of the invention can include formulations which have viscosities over a relatively wide range such as from 1 cS to 10,000 cS or more at about 20° C. and still deliver about 0.5 ml of formulation in less than about 1 second. This is obtained by utilizing a needle-free injector device with a nozzle having an opening and a length such that a range of volumes such as from 0.05 mL to 1.5 mL or more of formulation having the viscosity in the range of 1 cS to about 10,000 cS can be delivered out of the needle-free injector device through the nozzle and into the patient in about 1 second or less, more preferably less than about 0.1 second.

Another aspect of the invention is to employ a nozzle configuration in a needle-free injector that has a substantially larger orifice/length ratio than a needle, making it is possible to substantially reduce or eliminate the effects of viscous drag resulting from fully developed laminar flow and therefore safely, conveniently, and reproducibly deliver the injectate independent of formulation viscosity.

An aspect of the invention is to minimize the impact of viscosity on such delivery parameters as delivery time, rate of delivery, velocity of delivered medicament, penetration depth, and reproducibility of delivery. An aspect of the invention of obtaining delivery of high viscosity formulations is to use a needle-free injection constructed to allow for minimizing the ratio of orifice length to orifice exit diameter. This ratio

TABLE 1

Examples of peptide/protein controlled, release systems based on PLGA.

| Drug | Trade name | Company | Polymer | Route | Application |
|---|---|---|---|---|---|
| buserelin acetate | Profact ®Depot, Suprefact ®Depot | Hoechst Marion Roussel | PLGA | s/c implant | Prostate cancer |
| goserelin acetate | Zoladex☐Depot | Astra Zeneca | PLGA | s/c implant | Prostate cancer, endometrioses |
| leuprorelin acetate | Lupron ®Depot, Enantone ®Depot, Enantone ®Gyn Depot Trenantone ® | Takeda-Abbott | PLGA PLA | 3-month depot suspension, 1-month suspension 3-month suspension | Prostate cancer, endometrioses |
| octreotide acetate | Sandostatin LAR ®Depot | Novartis Pharma | PLGA | s/c suspension | GH suppression, anti cancer |
| triptorelin | Decapeptyl ® Depot | Debiopharma | PLGA | s/c depot injection | LHRH agonist, prostate cancer |
| recombinant human growth hormone | Nutropin ®Depot, [discontinued commercialisation since June 2004] | Genentech-Alkermes | PLGA | monthly s/c injection | Growth hormone deficiency |

Centipoise and centistokes are different measurements of viscosity, not just different units. Centipoise is a dynamic measurement of viscosity whereas centistoke is a kinematic measurement of viscosity. The conversion from centistoke and centipoise to s.i. units is given below:

1 cS=0.0001 m2/s  1 cP=0.001 Ns/m2

Invention in General

The invention includes needle-free injector devices which devices are loaded with containers which containers include high viscosity formulations comprised of pharmaceutically active drug wherein the high viscosity formulation is difficult may be less than 10, less than 7, less than 5, or about 2±20% or ±10% or ±5% for all ratios.

It is an aspect of the invention to deliver relatively viscous formulations for their sustained release (Depot) properties to patients suffering from disease states with treatments that benefit from a sustained release profile. Examples include compounds that require chronic injections, including but not limited to peptide and protein drugs. The use of sustained release formulation has the advantage of requiring fewer injections, leading to less pain, higher compliance, and less needle phobia.

One disease state that benefits greatly from sustained release, depot formulations is psychoses, including but not limited to schizophrenia and bi-polar disorder, including mania associated with bi-polar disorder.

Because psychotic states often lead to limited- or non-compliance with prescribed therapies, almost all anti-psychotic drugs benefit from a depot formulation. Examples of anti-psychotic drugs that benefit from the present invention include, but are not limited to Chlorpromazine, Fluphenazine, Mesoridazine, Perphenazine, Prochlorperazine, Promazine, Thioridazine/Sulforidazine, Trifluoperazine, Indoles (Molindone), Butyrophenones (Azaperone, Benperidol, Droperidol, Haloperidol), Thioxanthenes (Flupentixol, Chlorprothixene, Thiothixene, Zuclopenthixol), diphenylbutylpiperidines (Fluspirilene, Penfluridol, Pimozide), Loxapine) Butyrophenones (Melperone), Indoles (Sertindole, Ziprasidone), Benzamides (Sulpiride, Remoxipride, Amisulpride), diazepines/oxazepines/thiazepines (Clozapine, Olanzapine, Quetiapine), Aripiprazole, Risperidone, Paliperidone, Zotepine), including pharmaceutically acceptable salt and ester forms thereof. Combinations of two or more of these compounds, or combinations with other compounds.

Particularly preferred would be the use of the current invention in the treatment of schizophrenia or mania associated with bi-polar disorder as well as other conditions. The formulation would comprise one or more of Aripiprazole, Clozapine, Zyprasidone, Molindone, Quetiapine, Olanzapine, Risperidone, Paliperidone, Iloperidone, or pharmaceutically acceptable salts and ester forms thereof, and possibly in combination with other active ingredients.

In one embodiment, the formulation comprises a sustained release formulation of Risperidone. The amount of formulation delivered could be 10 micro-liters to 10 milliliters, preferably 0.25 to 2 milliliters, most preferably about 0.5 milliliter. Dosing frequency could be from weekly to 4 times yearly, preferably bi-weekly to bimonthly, most preferably monthly. The formulation could be stable for at least 6 months, preferably more than 1 year, most preferably 2 years or more.

In a preferred embodiment of the invention for the delivery of Resperidone and other active pharmaceutical ingredients, the depot is delivered using the needle free injector as described in U.S. Pat. Nos. 6,620,135, 6,554,818, 6,415,631, 6,409,032, 6,280,410, 6,258,059, 6,251,091, 6,216,493, 6,179,583, 6,174,304, 6,149,625, 6,135,979, 5,957,886, 5,891,086, and 5,480,381, incorporated herein by reference. Although many sustained release and depot formulations could be used with this injector for the delivery of Risperidone and other compounds, in a preferred embodiment, the formulation comprises sucrose acetate isobutyrate (SAIB) as described in U.S. Pat. No. 5,747,058.

The current invention describes various viscous formulations that can be delivered using a needle-free injector including the injector of U.S. Pat. No. 5,891,086 to provide for SC, ID, IM and other types of delivery. These formulations include various polymers, carriers, as well as API's in various physical forms.

An aspect of the invention is a method of injecting an animal, preferably a mammal, most preferably a human patient. The method includes loading a liquid formulation into a needle-free injector device. This loading can occur at the site of care, but is preferably performed at the factory. The formulation is comprised of a pharmaceutically acceptable drug in a carrier. The formulation has a viscosity as described herein, which viscosity is preferably about 5 cS or more at about 20° C. When the formulation is loaded into the needle-free injector about 0.1 ml of formulation or more of the formulation is extruded from the device in a narrow stream through an exit nozzle of the device. The stream is extruded at a rate of speed such that the stream punctures the skin of the patient such as a human patient. The 0.5 ml of formulation is extruded from the nozzle of the device through the skin in about 1 second or less, more preferably less than about 0.1 second.

The formulation may include particles such as microparticles and may include an agent which affects the viscosity of the formulation which may enhance the viscosity or decrease the viscosity as needed. Such viscosity enhancing agents are described within U.S. Pat. No. 6,667,061 and include compounds such as sodium carboxymethylcellulose. The formulation may also include wetting agents or other components which may generally be found within injectable formulations. The invention includes containers which are specifically designed for use in connection with needle-free injector devices which containers have loaded therein formulations of the invention which are particularly suitable for injection in a manner as described here. Some formulations are designed such that when the formulation is injected the viscosity of the formulation increases due to body temperature forming a solid or semi-solid implant within the patient. Such formulations are useful particularly with respect to providing controlled release of the drug contained within the formulation.

The global pharmaceutical market is growing rapidly. This growth is expected to continue and probably increase further. The genomics and proteomics revolutions, combined with huge advances in protein development, monoclonal antibodies and other areas, have meant that the market for injectable drugs is probably growing faster than most since the majority of these molecules are too large and/or fragile to be delivered by other methods such as orally.

Controlled release (CR) drug delivery systems are used to improve the therapeutic response by providing blood levels that are more therapeutically useful, and usually more consistent and stable compared to immediate release dosage forms. They can result in a reduction in adverse reactions since a) less drug may be required b) the drug may be targeted to the site in vivo avoiding high systemic levels, or c) lower peak plasma concentrations are required. As a consequence of targeted and controlled release, patient compliance may be improved due to lower dosing frequencies and simpler dosing regimens. With targeting and more controlled, sustained, predictable levels, efficacy may also be enhanced. CR parenteral drug delivery systems include but are not limited to: suspensions, liposomes, microspheres, gels, polymers, and implants. Tiny microspheres and larger implantable devices can be used to modify release over periods of months to years. These delivery systems are becoming increasingly utilized by the pharmaceutical industry to deliver drugs for treatment or prevention of a variety of diseases.

Furthermore, many pharmaceutical companies have developed or are developing sustained release formulations, to give a better pharmacological effect and/or a decreased frequency of injection.

However, it is difficult to formulate many of these molecules into stable solutions that are sufficiently concentrated to inject a reasonable sized dose (<1 ml). These formulations are also usually highly viscous—some are even gel-like with a viscosity of many Poise. This means that they are impractical to inject using a conventional needle and syringe.

Viscosity Versus Injection Time

A laboratory trial was performed to understand the difficulties of injecting viscous liquids using a needle and syringe and to determine whether the theory is applicable. Viscous fluids were forced through the needle using a hand-powered syringe and the injection time was recorded for a given applied force. Experimental details and results are described in detail in the example section.

Results from this study indicated that needle-free injectors with a nozzle that has a substantially larger orifice/length ratio as compared to a conventional needle, and are capable of delivering formulations at a high driving pressure, have the potential to deliver liquids that are thousands of times more viscous than those that can be delivered using a needle and syringe.

Improved Drug Release Profile for Surface Eroding Formulations

When injected with a needle and syringe, most depots will form a substantially spherical depot. In contrast, a needle-free injector can form a more spread out, complex form with a larger surface-to-volume ratio than a sphere. A spherical depot is less preferred for surface eroding systems, because as the depot erodes, the surface area decreases as the volume decreases. A preferred shape would be a sheet, or sheet-like shape. This type of shape would not substantially decrease in surface area as the depot erodes. Therefore, needle free injectors have the capability of actually improving the drug release kinetics of a depot, resulting in a more constant rate of drug release.

Examples of surface eroding systems include polymer families of polyanhydrides and poly(ortho esters) In 1985, Langer et. Al. developed the polyanhydride poly[bis(p-carboxyphenoxy)]propanesebacic acid (P(CPP:SA)), an extremely hydrophobic polymer with surface-controlled erosion. The polifeprosan 20 with carmustine implant (Gliadel® wafer) entered the U.S. market in 1996, and is today approved in several countries of the world. Studies have been reported where poly ortho esters were used for small molecule as well as macromolecule applications (Heller et al. European Journal of Pharmaceutics and Biopharmaceutics 50 (2000) 121±128, U.S. Pat. No. 6,667,371).

Pain During Injection

Pain and discomfort at the injection site may result in patients' refusal of depot injections. (J Clin Psychiatry. 2001 November; 62(11):855-9) The authors reported a study where long-acting depot injections of antipsychotic medications for patients suffering from schizophrenia were evaluated for pain. The depot injections caused pain, which was maximal immediately after the injection. A correlation existed between reported injection site pain and the effect it had on patients' attitude toward the depot injection as reported by the patients.

As per the package insert for Nutropin Depot, in studies involving 138 pediatric patients treated with Nutropin Depot, the most frequent adverse reactions were injection-site reactions, which occurred in nearly all patients. On average, 2 to 3 injection-site adverse reactions were reported per injection. These reactions included nodules (61% of injections), erythema (53%), pain post-injection (47%), pain during injection (43%), bruising (20%), itching (13%), lipoatrophy (13%), and swelling or puffiness (8%). The intensity of these reactions was generally rated mild to moderate, with pain during injection occasionally rated as severe (7%). Cooper et al. reported (Anaesthesia, Volume 55 Issue 3 Page 247, March 2000) significantly less pain on injection with the needle-free injector than with the 25G needle.

In a study that included comparing pain for needle-free and needle and syringe delivery, using a visual analogue scale, 60% of subjects reported no injection pain with the needle-free injector as compared to 30% of subjects with the needle and syringe. 41% of subjects reported pain levels of 4 or less, whereas 65% of subjects reported this degree of pain with needle and syringe (stout et al, Drug Delivery Technology, April 2004, Vol 4, No. 3).

Viscous Controlled Release Formulations

A number of specific compounds as well as generic descriptions of compounds which may be used in needle-free injector formulations are disclosed here. Further, numerous patents and publications which are incorporated herein by reference are disclosed for teaching other formulations which could be used in connection with the invention. However, it is important to note that the invention is directed towards high viscosity formulations and such high viscosity formulations are, in general, formulations which behave in a manner such as that shown within FIG. 3. Specifically, the formulation will have a viscosity at about 20° C. such that the viscosity is in a range of 1 to about 10,000 cS and can be delivered by needle-free injector device in about 1 second or less. Examples of specific formulations include those which have a viscosity in the range of 100 to about 10,000 cS at about 20° C. and those which can be delivered (0.5 ml) by a needle-free injector device in about 0.1 second or less. In general, when such formulations are administered by hypodermic needle injection, the injection requires about 10 seconds or more. Accordingly, the formulations and compounds described below should be reviewed and considered by those skilled in the art with consideration to obtaining the desired viscosity levels such that the formulation (0.5 ml) could be delivered using a needle-free injector device in about 0.1 second and could not be readily delivered by a hypodermic needle injecting device in such a short period of time or more specifically, those formulations wherein the hypodermic needle injector device requires more than 1 second, more than 2 seconds, more than 3 seconds, or more than 10 seconds to complete the injection.

An example of a sustained release polymer formulation that can be delivered by needle-free injection could use poly (ortho esters) as the vehicle. For example, see U.S. Pat. Nos. 4,304,767, 4,957,998, 5,968,543 and WO 02/092661 as well as Adv. Polymer Sci., 107, 41-92 (1993) and references therein. Viscosities of these controlled release polymers were reported to be in the 1,500 cP range (see Biomaterials, 23, 2002, 4397-4404). Considerably higher forces were required for higher molecular weight polymers (see Adv. Drug Del Reviews, 53, 2001, 45-73).

The invention may be used wherein the pharmaceutical agent is selected from a group consisting of antibodies or monoclonal antibodies, anti-inflammatory agents, antibacterial agents, antiparasitic agents, antifungal agents, antiviral agents, anti-neoplastic agents, analgesic agents, anaesthetics, vaccines, central nervous system agents, growth factors, hormones, antihistamines, osteoinductive agents, cardiovascular agents, anti-ulcer agents, bronchodilators, vasodilators, birth control agents and fertility enhancing agents, interferon alpha, osteoporosis drugs including PTH and PTH analogs and fragments, obesity drugs, psychiatric drugs, anti-diabetes, female infertility, AIDS, treatment of growth retardation in children, hepatitis, multiple sclerosis, migraine headaches, and allergic reactions.

The invention may be used wherein the pharmaceutical agent is a polypeptide or protein member selected from the group consisting of oxytocin, vasopressin, adrenocorticotropic hormone, epidermal growth factor, platelet-derived growth factor (PDGF), prolactin, luliberin, luteinizing hormone releasing hormone (LHRH), LHRH agonists, LHRH antagonists, growth hormone (human, porcine, bovine, etc.), growth hormone releasing factor, insulin, erythropoietin, somatostatin, glucagon, interleukin-2 (IL-2), interferon-.alpha.,.beta., or .gamma., gastrin, tetragastrin, pentagastrin, urogastrone, secretin, calcitonin, enkephalins, endorphins, angiotensins, thyrotropin releasing hormone (TRH), tumor necrosis factor (TNF), nerve growth factor (NGF), granulocyte-colony stimulating factor (G-CSF), granulocyte macrophage-colony stimulating factor (GM-CSF), macrophage-colony stimulating factor (M-CSF), heparinase, bone morphogenic protein (BMP), hANP, glucagon-like peptide (GLP-1), interleukin-11 (IL-11), renin, bradykinin, bacitracins, polymyxins, colistins, tyrocidine, gramicidins, cyclosporins and synthetic analogues, modifications and pharmacologically active fragments thereof, enzymes, cytokines, antibodies, vaccines and polymers, which may be copolymers or conjugates comprised of poly(ortho esters).

Formulations of the invention may include a polymer selected from the group consisting of but not limited to polylactic acid, poly glycolic acid, copolymers of lactic acid and glycolic acid and mixtures thereof or the formulation includes Formulations of the invention may include a polymeric material selected from the group consisting of but not limited to copolymers of lactic acid and glycolic acid, and mixtures thereof.

In one embodiment of the invention the formulation is capable of forming a depot. In one embodiment of the invention the formulation is in a polymeric, copolymeric or conjugated form using peptides or other conjugates wherein the polymers, copolymers or conjugates are comprised of methacralate or wherein said polymers, copolymers or conjugates are comprised of caprolactone or wherein said polymers, copolymers or conjugates are comprised of chitosan or wherein said polymers, copolymers or conjugates are comprised of polyanhydrides or wherein said polymers, copolymers or conjugates are comprised of polyethylene glycol or wherein said polymers or copolymers are comprised of polyphosphoesters or wherein said polymers, copolymers or conjugates are comprised of polyphosphazenes or wherein said polymers, copolymers or conjugates are comprised of dextran or other carbohydrates or sugars or wherein said polymers, copolymers or conjugates are comprised of dendrimers or other star polymers such as fullerenes or wherein said polymers, copolymers or conjugates are in a colloidal or suspension form or wherein said polymers, copolymers or conjugates are in a cross-linked form or present as crystals or nanocrystals or wherein said polymers, copolymers or conjugates are calcium phosphate particles or nanoparticles or wherein said polymers, copolymers or conjugates are comprised of polyetherester or wherein said polymers, copolymers or conjugates are comprised of hyaluronic acid or wherein said polymers, copolymers or conjugates are comprised of collagen or wherein said polymers, copolymers or conjugates are comprised of gelatin or wherein said polymers, copolymers or conjugates are comprised of dextran or wherein said polymers, copolymers or conjugates are comprised of amphiphiles or wherein said polymers, copolymers or conjugates are comprised of lipids and various physical agglomerates of lipids with or without polymer hybrids including but not limited to liposomes, hexagonal shapes or wherein said polymers, copolymers or conjugates are comprised of methacrylamides or wherein said polymers, copolymers or conjugates are comprised of polyethylene oxides or wherein said polymers, copolymers or conjugates are comprised of emulsifiable lipids or wherein the non-polymeric non-water soluble liquid carrier material is sucrose acetate isobutyrate or wherein said polymers, copolymers or conjugates are comprised of calcium phosphate or wherein it is comprised of but not limited to a polymeric, encapsulated, dispersed, suspended sugar or carbohydrate constituents or wherein the formulation is in an oil suspension or the formulation is in the form of liquid crystals.

Liposomes

Phospholipid vehicles as drug delivery systems were proposed as "liposomes" in 1965 by Bangham [Bangham et al., J. Mol. Biol. 13 (1) (1965) 238-252.]. In the early 90's, three products for intravenous injection entered the market: a liposomal preparation of amphotericin B (Ambisome®) for systemic fungal treatment, and two chemotherapeutic liposomal formulations: liposomal Doxirubicin (Doxil®) and liposomal Daunorubicin (Daunosome®).

Pegylated liposomes have been shown to have long circulating halflives. Vasopressin entrapped in PEGylated long-circulating liposomes remain bioactive one month after intravenous injection.

A new approach, rather than using unilamellar or multilamellar liposomes, is based on microscopic, spherical particles composed of hundreds of non-concentric aqueous chambers encapsulating the drug to be delivered. (DepoFoam™ system). These multivesicular liposomes (1-100 μm) contain multiple non-concentric internal aqueous compartments and lead to an increase in the encapsulation efficiency. After subcutaneous injection, the release of encapsulated peptide and protein was shown to be prolonged up to 7 days for Insulin and up to 3 weeks for the Leuprolide formulation [Ye, Q et al., DepoFoam technology, J. Control. Rel. 64 (1-3) (2000), 155-166.].

The company Novosom AG has patented a novel liposome-based depot system for proteins and peptides (Cagicles®). These depots are produced by a two step method: first, proteins are dissolved in an aqueous medium and then added to solutions of membrane-forming substances, which are selected such that the resulting membrane enters into a reversible mutual reaction with the protein. This mild-condition process enables to increase the encapsulation rate over 30% of incorporated protein. Furthermore, a one month sustained protein release was feasible after subcutaneous or intramuscular injection of the Cagicles depots [Panzner, S., Novosom A G, Application No. 2000-EP11079, Patent No. WO 2001034115 (2000)]. These studies have proven the basic applicability of liposomes. The solubility benefits of liposomes are well known and reported.

Lipid Nanoparticles and Microspheres

Solid lipid nanoparticles (SLNs) represent a colloidal carrier system mainly based on triglycerides. Due to their hydrophobic nature and their small size, SLNs may be more appropriate for incorporation of lipophilic drugs, which can be easily dissolved in the melted mixture. For instance, only small quantities of lysozyme can be incorporated into various lipids (Almeida et al, Int. J. Pharm. 149 (2) (1997) 255-265). Solid lipid nanoparticles own potential for the encapsulation of drugs with a low solubility (e.g. paclitaxel), for the application of surface-modified SLNs in drug targeting, or maybe for the use as adjuvant for vaccines. Furthermore, it can be hypothesised that SLNs can be applied for oral drug delivery in the form of aqueous dispersions or that they can alternatively be used as additives in traditional dosage forms such as tablets, capsules or pellets.

U.S. Pat. No. 6,277,413 describes a biodegradable microsphere having a matrix, the matrix comprising at least one type of biodegradable polymer, and at least one type of lipid; and a physiologically active substance which is releasable from the biodegradable microsphere.

Lipid Crystals

EP 0767,656B1 describes a pharmaceutical composition, which is glycerol-ester based and contains diacyl glycerol as well as phospholipid(s), or a polar group containing water, glycerol, ethylene glycol or propylene glycol. The proportions between the components are adjusted to form an L2 phase or a liquid crystalline phase, with the biological material being dispersed or dissolved in the L2 or liquid crystalline phase.

Oil Suspensions

Generally, the viscosity of oily media is considerably higher than the viscosity of an aqueous phase such as buffer. Therefore, drug release can be prolonged by implementing oil suspensions. In addition, the viscosity of the oily carrier can be further increased by the addition of gelling agents such as aluminium monostearate—thus enabling the control of process parameters like drug solubility and drug transfer rate. A further important aspect using oils as drug carrier refers to the distribution coefficient of compounds in the oily medium and the surrounding tissue. A lipophilic drug with a high distribution coefficient will primarily accumulate in the oily medium resulting in further deceleration of effective drug actions.

For several years, various peptides and proteins have been dispersed in oils to engineer sustained-release formulations. Nestor et al. patented as early as 1979 the development of long-acting injectable depot formulations for super-agonist analogues of luteinizing hormone-releasing hormone (LH-RH), applying oils such as peanut oil or sesame oil and a gelling agent such as aluminium stearate [Nestor et al, Syntex Inc., U.S. Pat. No. 4,256,737 (1979).].

Hydrogels

Thermoreversible hydrogels are of great interest in drug delivery. These include thermosensitive gel materials including poly(ethylene glycol)/poly(propylene glycol) block copolymers (poloxamers), poly(ethylene glycol)/poly(butylenes glycol) block copolymers, poloxamer-g-poly(acrylic acid) and copolymers of Nisopropylacrylamide that exhibit a sol-to-gel transition in aqueous solutions. Diblock copolymers of poly(ethylene oxide) (PEG) and poly(lactic acid) (PLA), and triblock copolymers of PEG-PLGA-PEG are also used as alternative hydrogels that would provide biodegradable and injectable drug-delivery systems under physiological conditions. Some natural polymers including gelatin, agarose, amylase, amylopectin, cellulose derivatives, carrageenans, and gellan, exhibit thermoreversible gelation behavior. Some cellulose derivatives of natural polymers, such as methyl cellulose and hydroxypropyl cellulose, exhibit reverse thermogelation behavior (gelation at elevated temperatures). Viscosity of these hydrogels is a concern for parenteral delivery. Viscosity of these hydrogels can be extremely high at low shear rates (Eur. J. of Pharm. and Biopharm., 59, 2005, 333-342). Poly hydroxyl methacralate is extensively used in hydrogel formulations (Peppas et al., European Journal of Pharmaceutics and Biopharmaceutics 50, 2000, 27). U.S. Pat. No. 6,602,952 describes a polymeric structure comprising a multifunctional poly(alkylene oxide), such as a poly(ethylene glycol) derivative, covalently cross-linked to a polymer selected from the group consisting of chitosan and conjugates of chitosan and a monofunctional poly(alkylene oxide), such as methoxy poly(ethylene glycol). In aqueous media, the polymeric structure forms a hydrogel.

Depot Formulations and Implantables

Implantable drug delivery devices provide an attractive therapeutic tool for treatment of a variety of diseases and conditions, especially when a sustained release effect is also added to the therapy. Various implantable drug delivery devices have been developed, and are based upon different mechanisms to accomplish movement of drug from a reservoir to the treatment site. U.S. Pat. No. 4,938,763 discloses a method for forming an implant in situ by dissolving a non-reactive, water insoluble thermoplastic polymer in a biocompatible, water soluble solvent to form a liquid, placing the liquid within the body, and allowing the solvent to dissipate to produce a solid implant. U.S. Pat. No. 5,747,058 describes a composition for the controlled release of substances that includes a non-polymeric non-water soluble high-viscosity liquid carrier material of viscosity of at least 5,000 cP at body temperature that does not crystallize neat under ambient or physiological conditions.

Delivery of Macromolecules

Protein formulations at high concentrations may also have physical properties that impact the ability to easily deliver the protein drug. For example, higher viscosity preparations may be difficult to administer by injection. Syringes for SC injection are often equipped with 26 or 27 gauge needles (J of Pharmaceutical Sciences, Volume 93, Issue 6, p 1390-1402).

Proteins such as monoclonal antibodies are often administered with frequent dosing regimens and at high doses (several mg/kg). Two antibodies, Rituxan1 and Herceptin1 that have been approved for the treatment of cancer are intravenously administered in hospitals, but several programs are underway for use of monoclonal antibodies to treat diseases that may require outpatient administration, and hence require the development of SC route of administration. Treatments with high doses, e.g., more than 1 mg/kg or 100 mg per dose, require development of formulations at concentrations exceeding 100 mg/mL because of the small volume (<1.5 mL) that can be given by the SC routes (J of Pharmaceutical Sciences, Volume 93, Issue 6, p 1390-1402).

U.S. Pat. No. 6,541,606 describes protein crystals or crystal formulations that are encapsulated within a matrix comprising a polymeric carrier to form a composition. The formulations and compositions enhance preservation of the native biologically active tertiary structure of the proteins and create a reservoir which can slowly release active protein where and when it is needed.

Conjugated Systems

Polymer carrier systems may have certain advantages over non-polymeric carriers in terms of avoiding uptake by macrophages. Because liposomes are spherical vesicles made of phospholipids are particles, they get taken up by macrophages. High levels can be found in the liver and spleen, even when the liposomes are given "stealth" characteristics by coating them with PEG. Antibodies, meanwhile, have the disadvantage that most receptors on tumor cells are also present on normal cells, making it hard to find ones that are unique to cancer.

In contrast, water-soluble polymers allow working with a single molecule rather than a large particle. To avoid the liver and spleen, uncharged hydrophilic polymers, such as PEG and N-(2-hydroxypropyl) methacrylamide can be used. When these polymers are hydrated, they can circulate in the blood for periods of up to about 24 hours (C&E News, Volume 80, Number 34, 39-47).

Examples of other conjugated systems include PEGylation. PEGylation decreases the rate of clearance from the bloodstream by increasing the apparent molecular weight of the molecule. Up to a certain size, the rate of glomerular filtration of proteins is inversely proportional to the size of the protein. Decreased clearance can lead to increased efficiency over the non-PEGylated material (see Conforti et al., Pharm. Research Commun. vol. 19, pg. 287, 1987 and Katre et al., Proc. Natl. Acad. Sci. U.S.A. vol. 84, pg. 1487, 1987). The conjugation could be either in-vitro or in-vivo.

WO2005034909A2 describes a hyperbranched polymer attached to a core and a biologically active moiety. The biologically active moiety is attached to the core by means of a substantially non-enzymatically cleavable linker L. The composition can be used to deliver the biologically active moiety to its target.

U.S. Pat. No. 6,946,134 describes therapeutic proteins fused to albumin or fragments or variants of albumin that exhibit extended shelf-life and/or extended or therapeutic activity in solution. The role of albumin as a carrier molecule and its inert nature are desirable properties for use as a carrier and transporter of polypeptides in vivo. The use of albumin as a component of an albumin fusion protein as a carrier for various proteins has been suggested in WO 93/15199, WO 93/15200, and EP 413 622. The use of N-terminal fragments of HA for fusions to polypeptides has also been proposed (EP 399 666).

U.S. Pat. No. 5,367,051 describes fullerene-functionalized amine-containing polymers and polymerizable monomers characterized by high temperature stability, i.e., capable of withstanding a temperature of at least about 300.degree. C., when in polymerized form. The fullerene groups are bonded to the polymers through the amine groups on the polymer.

WO Patent No. 2005073383 describes novel heterodimeric fusion proteins comprising a first polypeptide including an alpha subunit of FSH (aFSH) linked directly or indirectly to a binding partner of neonatal Fc receptor (FcRn) and a second polypeptide including a beta subunit of FSH (βFSH) linked directly or indirectly to an FcRn binding partner. The conjugated polypeptide has increased half-life and bioavailability as compared to traditional forms of FSH therapy.

Dendrimers

Dendrimers are well-defined polymeric structures. Dendrimers are based on repeating hyperbranched structures emanating from a central core (U.S. Pat. No. 4,507,466). Typical dendrimers are based on polyamidoamine (PAMAM), polyethylene imine (PEI), polypropylene imine or polylysine. These synthetic macromolecules are assembled in a stepwise fashion, with each reaction cycle adding another layer of branches (dubbed "generation"). Dendrimers are synthetically accessed by stepwise, divergent "bottom-up" or convergent "top-down" synthesis. Central structural component is the core unit from which hyperbranched dendrimers extend in a radially symmetric fashion. The core may provide at least two reactive groups for dendrimer conjugation, it may also be of heterofunctional nature and protecting groups may be used. In the latter case, the dendrimer may be assembled, and a guest compound may be subsequently conjugated to an anilin core by means of orthogonal chemistries (WO 88/01180). The core and dendrimers form the interior or backbone of a dendrimer. As a consequence of the spherical symmetry supported by sterical crowding, the terminal groups of the hyperbranches are defining the exterior. In higher generation dendrimers, the terminal branches form rather dense shells and flexible internal voids have been discovered. It is understood, that for a given dendrimer these cavities are filled up by backfolded end groups and tightly coordinated solvent molecules. Dendrimers are related to micelles, similary well suited to complex hydrophobic compounds. But in contrast they exhibit higher structural order because of their monomolecular nature and the absence of a dynamic equilibrium of various species. Synthetic compounds can only diffuse into dendrimers if certain structural requirement such as conformational rigidity and flatness as well as charge distribution such as affinity to tertiary amines are met. Various apolar compounds such as pyrene or naphthalene have been encapsulated in dendrimers.

In U.S. Pat. No. 5,714,166 and WO 95/24221, dendrimer-protein conjugates are revealed. PAMAM dendrimers of G4 are covalently coupled through their terminal functional groups to insulin, fluorescently labeled insulin, avidin, monoclonal antibodies and bradykinin. The reactive groups used for conjugation are only present at the surface of the dendrimers, and therefore any covalent adduct generated by the leached method will be associated with the dendrimer exterior.

PAMAM dendrimers contain free amine groups on their surfaces and readily associate with DNA through electrostatic interactions.

WO 01/07469 details water-soluble polypeptide dendrimers constituted of ornithin and glycine amino acids. The patent application also teaches the non-covalent encapsulation of an oligosaccharide, heparin, by dendrimerization of the dendrimer core in presence of heparin under mild conditions. The oligosaccharide is released from the dendrimer by light-induced cleavage of W-labile bonds within the dendritic backbone. The core structure used here was tris(2-maleimidoethyl)amine.

Other Polymeric Systems

Passirani et al. evaluated the use of heparin, dextran and methyl methacralate in a biomimetric approach in the development of drug carriers escaping early capture by phagocytosis (Passirani et al, Pharm Res, 1998, 15, 1046).

The synthesis of hybrid block and graft copolymers of polyphosphazenes and polystyrene is a way to combine the attributes of both polymers and generate new properties. Many of the valuable properties of the respective phosphazene and styrene homopolymers can be combined without sacrificing the overall solid state or solution properties of both polystyrene and polyphosphazene polymers. U.S. Pat. No. 6,392,008 describes such compositions of polyphosphazene-containing polymers.

U.S. Pat. No. 5,176,907 describes biocompatible and biodegradable poly(phosphoester-urethanes), compositions comprising the poly(phosphoester-urethanes), and methods of use as a drug delivery device and an implant.

Needle-Free Injectors

Specific injector devices which might be used with the present invention include, but are not limited to, injectors chosen from IntraJect®, Biojector 2000, Iject®, Intelliject, Injex, HSI 500, Medijector vision, Mini-Ject, Penjet®, Vitajet, PMED, Avant Guardian 101, Activa, Antares, Ypsomed, Medjet, The Medical house, Am-O-Jet™, Crossject™, DermoJet® & Vacci-Jet, Hyjettor™, IM-O-JET™, and an LectraJet™.

Needle-free injection of medications and vaccines represents an alternative route of administration that is as effective as needle and syringe but free of many of the problems. This method of injection utilizes a fine stream of medication at high pressure to penetrate the skin. The absence of hypodermic needles from the injection process removes the potential for needle-stick injuries and simplifies disposal, as well as removing a significant visual trigger for needle-phobia. The rapidity of needle-free injections (typically 0.5 second or less) further enhances patient compliance and acceptance.

Different needle-free injection devices in current use can be distinguished by the source of the power for injections—for example a spring, compressed gas, or a chemical reaction. Each of these designs has particular advantages and disadvantages.

Spring-powered devices have the advantage of being relatively inexpensive and durable. The disadvantages of this type of injector result from the limited amount of force that is generated by a coiled spring, which to some extent reduces the versatility of this class of injector.

Examples of spring-powered, needle-free injection devices include the Activa AdvantaJet, which is designed primarily for subcutaneous injection of 0.5-50 units of insulin. The Equidyne Injex is directed primarily at the diabetes market, and can deliver 0.02-0.5 ml of insulin subcutaneously. Use of the Injex for delivering vaccines is being explored as well (Sarno M J et al, 2000. Pediatr. Infect. Dis. J. 19:839-842). The Bioject/Vitajet 3 was originally developed for subcutaneous injection of insulin, and has recently been adapted by Serono as a delivery platform for their Saizen (Silverstein et al, 2001 Endocrine 15:15-17) and Serostim (Murray et al, 2001, Today's Therapeutic Trends 19:137-155) formulations of recombinant human growth hormone. Needle-free delivery of growth hormone has considerable appeal from the perspective of acceptance and compliance in the paediatric market (Saizen) and improved safety for injecting HIV-positive patients (Serostim).

The Antares/Medi-Jector VISION is a spring-powered device intended for subcutaneous injections of 2 to 50 units of insulin (Bremseth et al, 2001, Diabetes Technol. Ther. 3:225-232). Medi-Ject devices have also proven to be effective in delivering other medications (Verrips et al, 1998, Acta Paediatr. 87(2):154-8) and DNA vaccines (Anwer et al., 1999, Pharm. Research 16:889-895). The Medi-Jector VISION uses a replaceable transparent needle-free syringe, which is available in three orifice sizes. Changing the orifice size modulates the injection pressure to accommodate differences in the thickness and penetrability of various skin types and anatomical locations. Other similar Medi-Jector devices are marketed for administering recombinant human growth hormone (G H, Hirasing et al., 1998 Acta Paediatr. 87(2):154-8).

Gas-powered devices present the advantages of the more sustained force provided by compressed gas relative to a coiled spring. Thus, larger volumes of injection (up to 1.0 ml) can be administered via either the subcutaneous or intramuscular route. The primary disadvantage of gas-powered devices is that, unlike a spring, the source of power is exhaustible and must therefore be replaced periodically.

Examples of gas-powered injection devices include the CO2-powered Biojector 2000, the advantages of which include versatility, as it can provide IM and SQ injections of volumes ranging from 0.1 to 1.0 ml (Stout R, Miller R, 1997). Visionary Medical Products manufactures the PenJet, a small disposable injector that uses pre-filled ampoules to deliver up to 0.5 ml of medication. Activation of the device is pressure-sensitive, which ensures that the user applies the appropriate amount of force when administering an injection. To provide increased convenience, National Medical Products has developed the J-Tip, a CO2-powered disposable injector designed to deliver subcutaneous injections of 0.02 to 0.25 ml of insulin. Injection of lidocaine and low molecular weight heparin with the J-Tip has been evaluated as well (Hollingsworth S J et al., 2000. Ann. R. Coo. Surg. Eng. 82:428-431).

U.S. Pat. No. 5,911,703 describes a two-stage jet injector of the present invention includes, in combination, a syringe unit, a drive mechanism for advancing the syringe plunger in a two-stage sequence, and a suction compartment which surrounds an injection tube of the syringe. The drive mechanism includes a push rod which is positioned longitudinally co-linear with the plunger of the syringe, when the syringe unit is operably connected to the drive mechanism. Accordingly, advancement of the plunger into the syringe chamber is caused by movement of the push rod. In accordance with the present invention, the push rod is driven by two separate springs, which are engaged with the push rod, and which are coaxially positioned around the push rod. Specifically, the first of the two coaxial springs is an impulse spring which is characterized by a relatively high spring constant and the fact that it is dimensioned to have a relatively short action distance. In comparison with the first spring, the second spring, a perfusion spring, has a lower spring constant and a longer action distance.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Viscosity Versus Injection Time

Two trials were undertaken to determine the injection time of viscous fluids with both Intraject and a needle and syringe. The viscous fluids used in the trials were a range of different viscosity Dow Corning silicone oils. For the needle and syringe a range of the fluids were ejected by hand and the times recorded, for Intraject an instrumented force sensor was used to measure injection time for all available viscosities, however high-speed video was used for the thickest of the fluids because they did not flow properly off the force sensor and so did not give useable readings.

For the needle trial a 3 ml syringe and a 23G needle were used; the needle had an internal diameter of 0.38 mm and was the closest available needle size to that of the Intraject orifice (0.3 mm). The needle had a length of 31 mm and the syringe had an internal cross-sectional area of 58.5 $mm^2$. Liquid formulation in an amount of 0.5 ml with viscosities of 50, 100, 500 and 1,000 cS were ejected from the needle and syringe by hand and the times taken were recorded and averaged. As much force as possible was applied by hand to the syringe and a similar force was applied to all the oils used. However, with the thinner fluids it was hard to apply as large a force as with the thicker ones because the syringe plunger was moving faster. When a similar force was applied to a load cell about 15N was recorded.

An Intraject needle-free device was used which included a standard Ø0.3 mm orifice. The same orifice was used for all the firings to remove any variations that may arise from differences between orifi. Liquid formulations in an amount of 0.5 ml with viscosities of 1, 5, 10, 20, 50, 100, 500 and 1,000 cS were used in each device. To determine the injection time of both the 12,500 cS and 30,000 cS fluids high-speed video was used.

Figure 3:
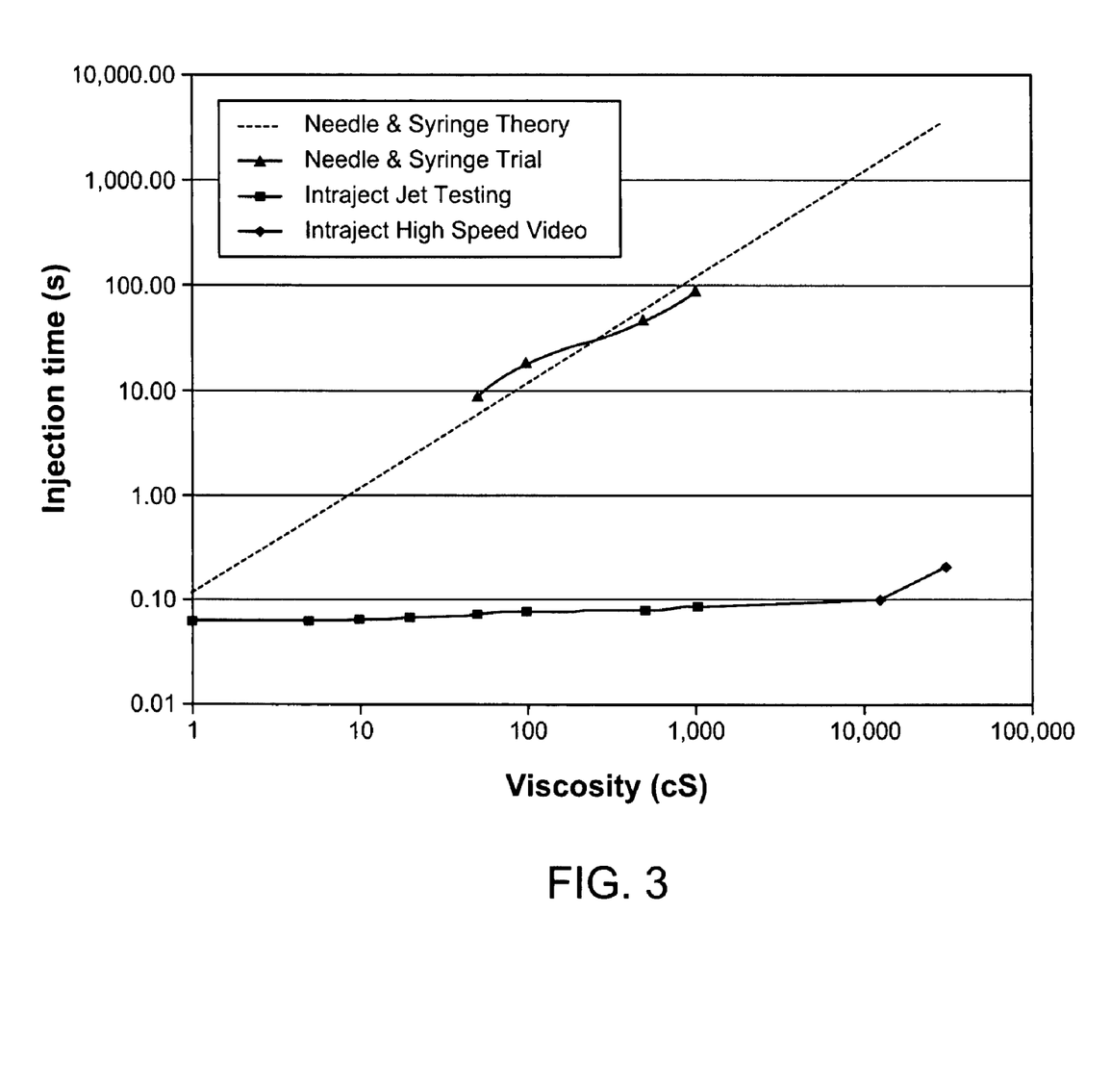
FIG. 3 is a graph showing the injection times of a needle & syringe against the needle-free injector; both axes are using logarithmic scales.

Both sets of injection time data have been plotted together in FIG. 3. However, because of the large differences in injection times for a needle and Intraject the only way to see both lines clearly is to plot the graph using logarithmic scales for both axes. Using the theory for fully developed flow and a force of 15N the theoretical time to inject 0.5 ml of the viscous liquids was calculated and also plotted.

Figure 1:
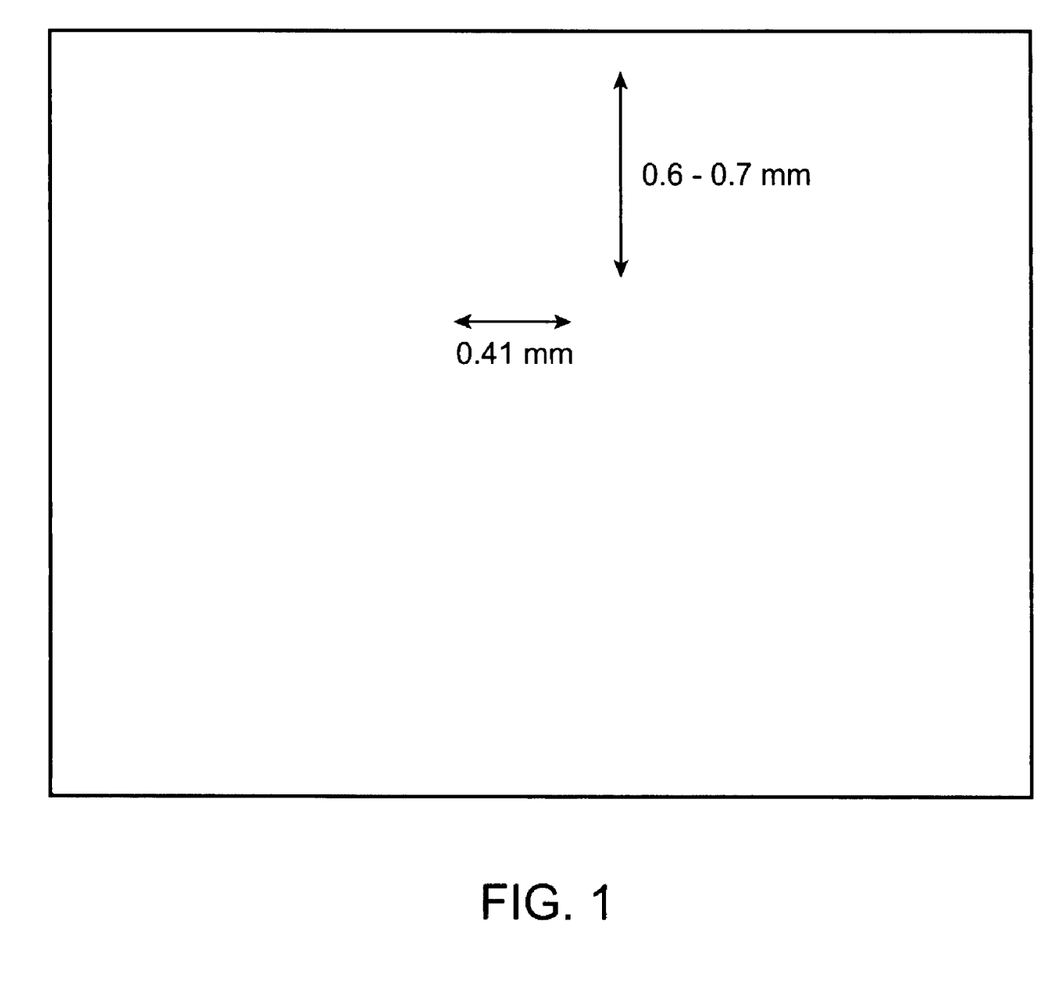
FIG. 1 is an image showing the dimensions of hole length and critical length (typically diameter) for the exit opening of the nozzle of the needle-free injector in this figure, the ratio of hole length to diameter is in a range of 1.5 to 1.7±20%. At that ratio, for viscosities less than ~10,000 cS, viscous losses are negligible.
Figure 2:
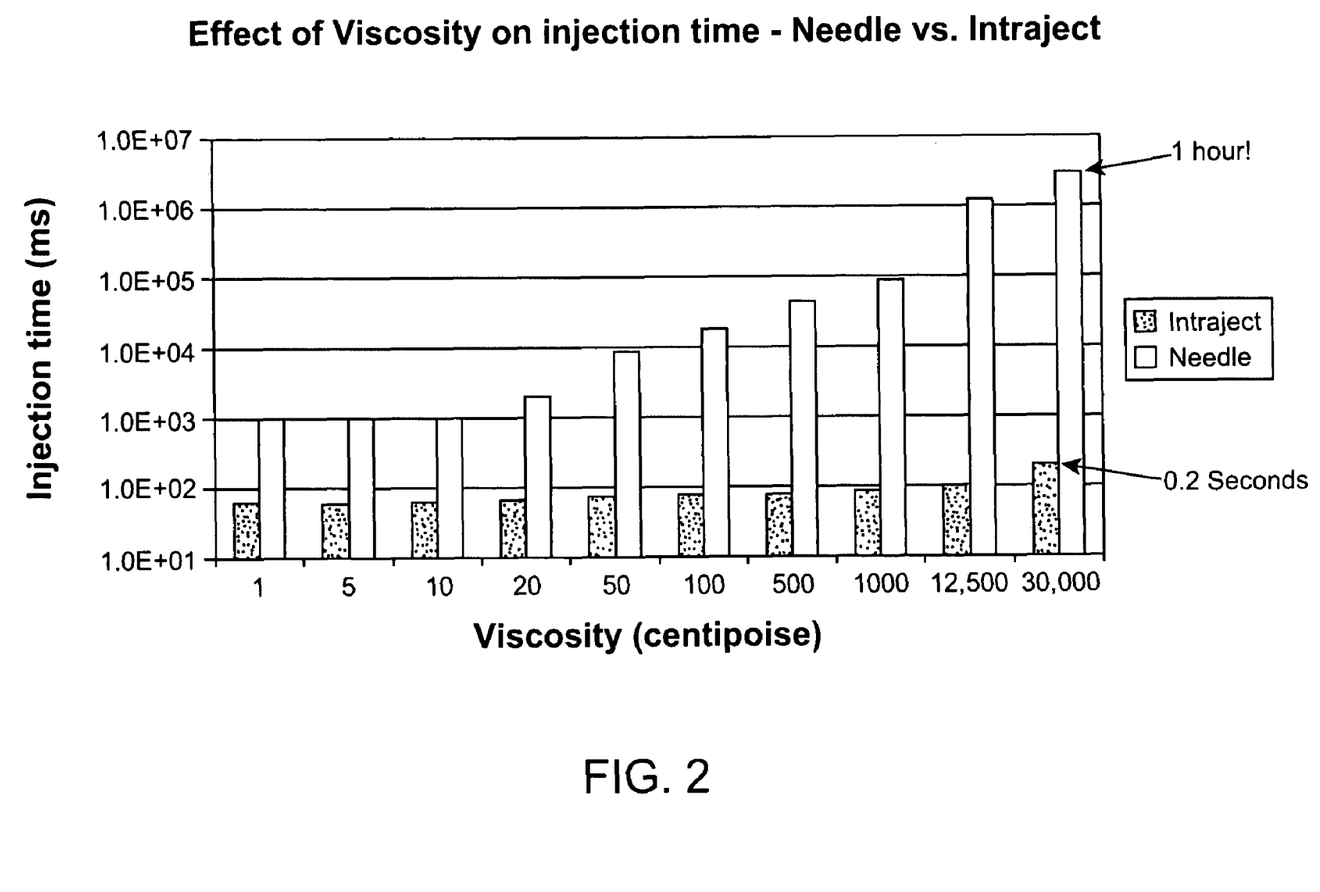
FIG. 2 is a graph showing the effect of viscosity on injection time for a needle with length to diameter ratio of 22.2 (white) versus Needle-free with a length to diameter ratio of 2.3 (black) delivery. Both methods delivered 0.5 mL of non-thixotropic fluid. Needle injections were using 23G needle, with maximum hand force that could be applied by tester (approx. 20 N/5 lbF).

The key results were (see FIGS. 2 and 3):

A 23G needle, 31 mm long, would take 90 seconds to inject 0.5 ml of a 1,000 cS solution with the user applying as much force as possible with their thumb on the end of the syringe (approx 15N). This compares to less than a second for a drug with the viscosity of water.

By contrast, Intraject took 0.085 seconds to deliver a 1,000 cS solution.

The injection time for highly viscous fluids can be extrapolated from trial data. For Intraject this gave a 1 second delivery time with 0.5 ml of 150,000 cS fluid and 7 seconds for a 1,000,000 cS fluid. Using a 23G needle and syringe with these fluids would give injection times of 5 hr and 33 hr respectively.

There are two reasons for the difference in performance. Firstly an Intraject nozzle is considerably shorter than the needle, which means that viscous flow does not have a chance to develop. Secondly, the driving pressure in Intraject is much greater than in a needle and syringe, this leads to a faster flow of liquid and a shorter injection time.

The application of fully developed laminar pipe flow theory allows us to predict the injection times for different combinations of needle lengths and diameters, as well as understand the limits of Intraject with highly viscous fluids.

Results from this study indicate that needle-free injectors with a nozzle that has a substantially larger orifice/length ratio than a needle, and/or capable of delivering formulations at a high driving pressure, have the potential to deliver liquids that are thousands of times more viscous than those that can be delivered using a needle and syringe.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A needle-free device, comprising:
    a container having therein a formulation having a viscosity of 100 cS or more at 20° C., the formulation comprising a pharmaceutically acceptable carrier and a pharmaceutically active drug;
    an injector comprised of a channel and power source, the channel having a channel length to exit opening diameter ratio of 1.7±20%; and
    wherein the power source comprises sufficient power to extrude the formulation through the channel at a rate of 5,000 microliters or more per second.

2. The device of claim 1, wherein the formulation has a viscosity of 1,000 cS or more at 20° C.

3. The device of claim 1, wherein the power source is selected from the group consisting of a spring, compressed gas, and a chemical reaction.

4. A needle-free device, comprising:
    a container having therein a formulation having a viscosity of 1,000 cS or more at 20° C., the formulation comprising a pharmaceutically acceptable carrier and a pharmaceutically active drug;
    an injector comprised of a channel and power source, the channel having a channel length to exit opening diameter ratio of 1.7±20%; and
    wherein the power source comprises sufficient power to extrude the formulation through the channel at a rate of 5,000 microliters or more per second;
    wherein the pharmaceutically active drug is selected from the group consisting of Aripiprazole, Clozapine, Zyprasidone, Molindone, Quetiapine, Olanzapine, Risperidone, Paliperidone, Iloperidone, and pharmaceutically acceptable salts and ester forms, and combinations thereof.

* * * * *